US008658582B2

(12) United States Patent
Cao et al.

(10) Patent No.: US 8,658,582 B2
(45) Date of Patent: *Feb. 25, 2014

(54) CLEAR COSMETIC COMPOSITIONS CONTAINING LIPOPHILIC MATERIALS

(75) Inventors: Hongjie Cao, Ringoes, NJ (US); Dina Burakov, Edison, NJ (US)

(73) Assignee: L'oreal, Paris (FR)

( * ) Notice: Subject to any disclaimer, the term of this patent is extended or adjusted under 35 U.S.C. 154(b) by 87 days.

This patent is subject to a terminal disclaimer.

(21) Appl. No.: 12/961,583

(22) Filed: Dec. 7, 2010

(65) Prior Publication Data
US 2012/0142569 A1 Jun. 7, 2012

(51) Int. Cl.
| | |
|---|---|
| C11D 3/60 | (2006.01) |
| C11D 1/06 | (2006.01) |
| C11D 1/12 | (2006.01) |
| A61K 8/31 | (2006.01) |
| A61K 8/36 | (2006.01) |
| A61K 8/37 | (2006.01) |
| A61K 8/45 | (2006.01) |
| A61Q 5/00 | (2006.01) |
| A61Q 5/12 | (2006.01) |

(52) U.S. Cl.
USPC ........... 510/119; 510/130; 510/159; 510/405; 510/421; 510/422; 510/437; 510/488; 424/70.1; 424/70.19; 424/70.21; 424/70.22; 424/70.31

(58) Field of Classification Search
USPC ........ 510/119, 130, 159, 405, 421, 422, 437, 510/488; 424/70.1, 70.19, 70.21, 70.22, 424/70.31
See application file for complete search history.

(56) References Cited

U.S. PATENT DOCUMENTS

| | | | | |
|---|---|---|---|---|
| 5,417,965 | A | * | 5/1995 | Janchitraponvej et al. ... 510/122 |
| 5,747,435 | A | | 5/1998 | Patel |
| 5,747,436 | A | * | 5/1998 | Patel et al. .................... 510/124 |
| 6,274,128 | B1 | * | 8/2001 | Bergmann et al. ........... 424/70.1 |
| 6,306,805 | B1 | * | 10/2001 | Bratescu et al. .............. 510/123 |
| 6,440,437 | B1 | * | 8/2002 | Krzysik et al. ................ 424/402 |
| 7,378,479 | B2 | * | 5/2008 | Tamareselvy et al. ........ 526/333 |
| 7,699,897 | B2 | | 4/2010 | Nguyen et al. |
| 2004/0266645 | A1 | * | 12/2004 | Albrecht et al. .............. 510/395 |
| 2005/0271595 | A1 | * | 12/2005 | Brown ......................... 424/10.1 |
| 2006/0024256 | A1 | | 2/2006 | Wells et al. |
| 2008/0095726 | A1 | * | 4/2008 | Nguyen et al. ................ 424/70.7 |
| 2009/0053161 | A1 | * | 2/2009 | Nguyen et al. ............. 424/70.17 |
| 2009/0071493 | A1 | | 3/2009 | Nguyen et al. |
| 2009/0071494 | A1 | | 3/2009 | Nguyen et al. |
| 2009/0074683 | A1 | | 3/2009 | Nguyen et al. |
| 2009/0074700 | A1 | | 3/2009 | Nguyen et al. |
| 2010/0202988 | A1 | * | 8/2010 | Nguyen et al. .................. 424/59 |
| 2010/0202995 | A1 | * | 8/2010 | Nguyen et al. ................ 424/70.1 |
| 2010/0202996 | A1 | * | 8/2010 | Cannell et al. ............... 424/70.5 |
| 2010/0322876 | A1 | | 12/2010 | Nguyen et al. |

FOREIGN PATENT DOCUMENTS

EP 2216011 A2 8/2010

OTHER PUBLICATIONS

John A. Wenninger, G.N. McEwen, Jr., International Cosmetic Ingredient Dictionary and Handbook, 1997, 7th Edition, Cosmetic, Toiletry and Fragrance Association (CTFA), 1101 17th Street, N.W., Suite 300, Washington, D.C. 20036-4702, USA.
International Search Report, International Application PCT/EP2011/071933, mailed on Aug. 12, 2013.
Amendment filed for U.S. Appl. No. 13/728,301 on Sep. 4, 2013.

\* cited by examiner

Primary Examiner — Lorna M Douyon
(74) Attorney, Agent, or Firm — L'oreal USA

(57) ABSTRACT

The present invention is directed toward a composition comprising: (a) at least one alkoxylated monoamine; (b) at least one alkoxylated monoacid; (c) at least one lipophilic compound; (d) at least one surfactant; (e) optionally, at least one auxiliary ingredient; and (f) at least one cosmetically acceptable carrier; wherein the ratio by weight of (b):(a) is greater than 1 and wherein the ratio by weight of (a)+(b):(c) is greater than 2. The present invention also relates to methods for cleansing and conditioning keratinous substrates. The methods can provide hair with improved shine, condition, manageability, and styling ability.

9 Claims, No Drawings

CLEAR COSMETIC COMPOSITIONS CONTAINING LIPOPHILIC MATERIALS

FIELD OF THE INVENTION

The present invention relates to personal care and cosmetic compositions. In particular, the present invention relates to compositions that are clear in appearance and methods of cleansing and conditioning keratinous substrates using such clear compositions.

BACKGROUND OF THE INVENTION

Cosmetic and personal care products are available in various forms and one of the forms that are desired by many consumers is a clear aqueous product. At the same time, the consumer expects that such a product will provide desirable cosmetic benefits to keratinous substrates such as hair and skin.

Further, consumers prefer products that can serve more than one function. For example, with respect to hair care, consumers generally prefer a product that can clean and condition their hair in a single step. Such dual functionality can often be found with water insoluble ingredients, such as, for example, oils that condition the hair.

A sufficient amount of such oils is required to condition hair or skin. However, it has been difficult to provide clear personal care compositions that incorporate such amounts so that the compositions can serve more than one function.

Certain water-insoluble ingredients, which are oftentimes desirable for the treatment of keratinous substrates, are inherently difficult to incorporate into aqueous systems, such as shampoos, conditioners and skin care compositions, without forming a traditional emulsion in either cream or lotion form. Oftentimes, the presence of such ingredients at levels that would impart appreciable cosmetic benefits to hair or skin and/or properties to cosmetic and personal care products result in unstable formulations resulting in undesirable phase separations in aqueous systems.

Therefore, in the formulation of clear aqueous compositions, water-insoluble compounds do not lend themselves to being used therein, due to their inability to significantly associate with the water present in the system. As a result, the presence of these water-insoluble ingredients is generally minimal in personal care products and cosmetic products that employ aqueous systems. Thus, the difficulties in formulating such compositions deprives the consumer of products that can better deliver cosmetic benefits to hair and skin such as conditioning, cleansing, coloring of hair, styling of hair, skin care, and better application and spreadability of products.

Thus, it is desirable to provide clear compositions, such as cleansing compositions that incorporate oils in order to provide multiple cosmetic benefits to keratinous substrates. It is also desirable to provide methods of cleansing and conditioning keratinous substrates with such compositions.

SUMMARY OF THE INVENTION

The present disclosure is directed to a composition comprising:
(a) at least one alkoxylated monoamine;
(b) at least one alkoxylated monoacid;
(c) at least one lipophilic compound;
(d) at least one surfactant;
(e) optionally, at least one auxiliary ingredient; and
(f) at least one cosmetically acceptable carrier;
wherein the ratio by weight of (b):(a) is greater than 1 and wherein the ratio by weight of (a)+(b):(c) is greater than 2.

The present invention further relates to methods for cleansing and conditioning a keratinous substrate comprising applying the above-described composition to the keratinous substrate.

It has been surprisingly and unexpectedly discovered that the use of these clear compositions on keratinous substrates, such as hair and skin, results in desirable and beneficial effects on the substrates, for example, delivery of active ingredients, cleansing, conditioning, hair styling effects, manageability, improved shine, protection from environmental and chemical damage, and enhanced color and cosmetic effects.

DETAILED DESCRIPTION

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about," meaning within 10% to 15% of the indicated number.

The term lipophilic compound means those compounds which are soluble in oils and other non-polar solvents and are either completely or partially insoluble in water.

"At least one" as used herein means one or more and thus includes individual components as well as mixtures/combinations.

The term "clear" as used herein means transparent such that a person is able to see through the composition with their naked eye. The term "clear" as used herein also means that the composition does not exhibit phase separation. The term "clear" as used herein also means that the composition has visible light transmissions of at least 70 percent when measured using a commercial spectrophotometer. The term "clear" as used herein is not meant to encompass those compositions which a person cannot see through with their naked eye such as those which are pearlescent, frosted, hazy, opaque, or cloudy in appearance.

The term "silicone free" means the compositions are substantially free (that is, less than 0.25%), essentially free (that is, less than 0.1%), or free (that is, 0%) of silicones.

The term "sulfate free" means the compositions are substantially free of sulfate-based anionic surfactants (that is, less than 0.25%), essentially free of sulfate-based anionic surfactants (that is, less than 0.1%), or free (that is, 0%) of sulfate-based anionic surfactants.

The term "lipophilic carrier system" means a system that will deliver a lipophilic compound into an aqueous phase by incorporation or solubilization. The lipophilic carrier system is capable of bringing a lipophile into an aqueous phase such that the aqueous phase remains clear. The lipophilic carrier system includes alkoxylated monoamines and alkoxylated monoacids.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Alkoxylated" as used herein means —O—CHR—(CH2)n- wherein R represents H or an alkyl group, and wherein n≥1.

Alkoxylated Monoamines

Non-limiting examples of suitable alkoxylated monoamines include compounds corresponding to the formula (I):

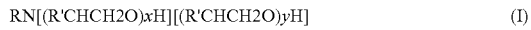

RN[(R'CHCH2O)xH][(R'CHCH2O)yH]    (I)

wherein R is linear or branched, acyclic or cyclic, saturated or unsaturated, aliphatic or aromatic, substituted or unsubstituted hydrocarbon radical containing at least 6 carbon atoms;

x and y, independently of one another, represent numbers of from 0 to 100;

R' represents hydrogen, or an alkyl group; and the sum of x+y is >0.

In formula (I), R is linear or branched, acyclic or cyclic, saturated or unsaturated, aliphatic or aromatic, substituted or unsubstituted. Typically, R is a linear or branched, acyclic alkyl or alkenyl group or an alkyl phenyl group; x and y, independently of one another, is typically a number from 2 to 30, more typically a number from 1 to 25 and most typically a number from 0 to 15.

Examples of the alkoxylated monoamines for use in the present invention which correspond to formula (I) are PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding to formula (II):

RNR"[(R'CHCH2O)xH]    (II)

wherein R is a hydrocarbon radical containing at least 6 carbon atoms;

x represents a number of from 1 to 100;

R' represents hydrogen, or an alkyl group; and

R" is a hydrogen or a hydrocarbon radical.

In formula (II), R is linear or branched, acyclic or cyclic, saturated or unsaturated, aliphatic or aromatic, substituted or unsubstituted. Typically, R is a linear or branched, acyclic alkyl or alkenyl group or an alkyl phenyl group; x is typically a number from 1 to 30, more typically a number from 0 to 25 and most typically a number from 0 to 15.

When R" in formula (II) is a hydrocarbon radical group, this group may be linear or branched, saturated or unsaturated, substituted or unsubstituted. The hydrocarbon radical represented by R" may also contain an alkoxylated moiety (as defined by [(R'CHCH2O)yH]), and/or heteroatoms such as nitrogen. When R" contains at least one alkoxylated moiety, the total number of alkoxylation in the formula may range from 1 to 120.

Examples of alkoxylated monoamines for use in the present invention which correspond to formula (II) are PEG-3 Tallow Aminopropylamine, PEG-10 Tallow Aminopropylamine, PEG-Tallow Aminopropylamine, and PEG-105 Behenyl Propylenediamine.

Additional non-limiting examples of alkoxylated monoamines include compounds corresponding to formula (III):

R(R'CHCH2O)x(R'CHCH2O)yNH2    (III)

wherein R is linear or branched, acyclic or cyclic, saturated or unsaturated, aliphatic or aromatic, substituted or unsubstituted hydrocarbon radical containing at least 6 carbon atoms;

x and y, independently of one another, represent numbers of from 0 to 100;

R' represents hydrogen, or an alkyl group; and the sum of x+y is >0.

In formula (III), R is linear or branched, acyclic or cyclic, saturated or unsaturated, aliphatic or aromatic, substituted or unsubstituted. Typically, R is a linear or branched, acyclic alkyl or alkenyl group or an alkyl phenyl group; x and y, independently of one another, is typically a number from 2 to 30, more typically a number from 1 to 25 and most typically a number from 0 to 15.

Examples of alkoxylated monoamines for use in the present invention which correspond to formula (III) are polyetheramines containing a monoamine group. These polyetheramines are commercially available from Hunstman under the tradenames Jeffamine (M series such as M-600, M-1000, M-2005 and M-2070) and Surfonamine series (B-60, B-100, B-200, L-100, L-200, L-207, L-300).

The at least one alkoxylated monoamine is present in the composition in an amount of from about 0.1 to about 4% by weight, such as from about 0.1 to about 2% by weight, and from about 0.5 to about 1% by weight, including all ranges and subranges there-between, based on the total weight of the composition.

Alkoxylated Monoacids

Non-limiting examples of alkoxylated monoacids include compounds corresponding to formula (IA):

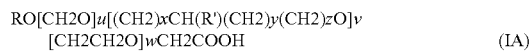

RO[CH2O]u[(CH2)xCH(R')(CH2)y(CH2)zO]v[CH2CH2O]wCH2COOH    (IA)

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z is ≥0;

Compounds corresponding to formula (IA) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (IA), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids of the present invention include, but are not limited to, the following representatives referred to by their INCI names (INCI: nomenclature for raw materials according to the International Cosmetic Ingredient Dictionary, 7th Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof.

The at least one alkoxylated monoacid is present in the composition in an amount of from about 0.1 to about 6% by weight, such as from about 0.5 to about 4% by weight, and from about 1 to about 2% by weight, including all ranges and subranges there-between, based on the total weight of the composition.

A preferred ratio by weight of the at least one alkoxylated monoacid to the at least one alkoxylated monoamine of the present invention is greater than 1.

Lipophilic Compound

The at least one lipophilic compound may, for example, be chosen from oils, fatty esters, hydrocarbon oils, waxes, fatty acids and salts thereof, fatty alcohols, lipophilic vitamins and esters thereof, organic sunscreens, phospholipids, and mixtures thereof.

Non-limiting examples of oils include plant oils such as olive oil, avocado oil, coconut oil, safflower oil, almond oil, castor oil, jojoba oil, peanut oil, sesame oil, hazelnut oil, sunflower oil, apricot kernel oil, grapeseed oil, palm oil, argan oil, squalane and pracaxi oil.

Non-limiting examples of synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, isoparaffins, isododecanes, aromatic hydrocarbons, and mixtures thereof.

Non-limiting examples of waxes include paraffin wax, beeswax, candelilla wax, carnauba wax, jasmine wax, jojoba wax and mimosa wax.

Suitable fatty acids include those containing from 8 to 30, preferably from 12 to 24 carbon atoms, and carboxylate salts of fatty acids. The sodium, potassium, ammonium, calcium and magnesium carboxylates of fatty acids listed are typical examples of the carboxylate salts of the fatty acids.

Non-limiting preferred examples of fatty alcohols include compounds of formula:

where R represents a hydrocarbon radical containing at least three carbon atoms, preferably from 8 to 30, more preferably from 12 to 24 carbon atoms, and which may be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Non-limiting preferred fatty esters include esters formed from fatty acids and $C_{1-10}$ alcohols and esters formed from the fatty alcohols as defined hereabove and $C_{1-10}$ carboxylic acids.

In addition, non-limiting specific examples of lipophilic compounds include isopropyl palmitate, capric/caprylic triglyceride, isodecyl neopentanoate, polyIsobutylene, Phloretin, Ellagic acid, Vitamin D, Vitamin E, Vitamin E Acetate, Vitamin A, Vitamin A Palmitate, 2-oleamido-1,3-octadecanediol, octyl methoxycinnamate, octyl salicylate, 18-Methyleicosanoic acid, and mixtures thereof. Other types of lipophiles include organic sunscreens, phospholipids, other water-insoluble vitamins, and other natural and synthetic oils.

According to a preferred embodiment, the at least one lipophilic compound is chosen from plant oils, hydrocarbon oils, synthetic oils, fatty acids having at least 12 carbon atoms, fatty esters and mixtures thereof.

The at least one lipophilic compound is present in the composition in an amount of from about 0.1 to about 2% by weight, such as from about 0.3 to about 1.5% by weight, and from about 0.5 to about 1.0% by weight, including all ranges and subranges there-between, based on the total weight of the composition.

The ratio by weight of the alkoxylated monoacids to the alkoxylated monoamines to the lipophilic compounds is preferably at about 2:1:1, but may be present in other ratios such as at about 1.5:1:1, at about 3:1:1, at about 4:1:1 and at about 5:1:1.

A preferred ratio by weight of the sum of the at least one alkoxylated monoamine and the at least one alkoxylated monoacid to the at least one lipophilic compound of the present invention is greater than 2.

Surfactant

The compositions also contain at least one surfactant selected from nonionic surfactants, anionic surfactants, amphoteric surfactants, zwitterionic surfactants and mixtures thereof.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from about 1 to about 110 alkoxy groups. The alkoxy groups are selected from the group consisting of C2-C6 oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed hereinabove.

Commercially available nonionic surfactants are Brij® nonionic surfactants from Croda, Inc., Edison, N.J. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, which are the condensation products of long chain alcohols, e.g. C8-C30 alcohols, with sugar or starch polymers. These compounds can be represented by the formula (S)n —O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryloleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups are selected from the group consisting of C2-C6 oxides and their mixtures, with ethoxylated or propoxylated derivatives of these materials being typical. Nonlimiting examples of commercially available ethoxylated materials include TWEEN® (ethoxylated sorbitan mono-, di- and/or tri-esters of C12 to C18 fatty acids with an average degree of ethoxylation of from about 2 to 20).

Non-limiting examples of anionic surfactants include compounds in the classes known as alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, isethionates and mixtures thereof. Specific examples of anionic surfactants include the ammonium, monoethanolamine, diethanolamine, triethanolamine, isopropylamine, sodium, potassium, lithium, or magnesium salts of dodecylbenzene-sulfonate, lauryl sulfosuccinate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alky amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures; and/or nonionic surfactants such as, but not limited to, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccarides, polysiloxane polyethoxylene ether and mixtures thereof. Specific examples include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate and mixtures thereof.

The at least one surfactant is typically present in an amount from about 0.1 by weight to about 45% by weight, typically in an amount from about 5 by weight to about 30% by weight and more typically from about 10 by weight to 20% by weight, including all ranges and subranges there-between, based on the total weight of the composition.

Auxiliary Ingredients

The composition may optionally contain at least one auxiliary ingredient. The auxiliary ingredients may include in particular, film forming agents, proteins, amino acids, conditioning agents, cationic polymers, skin and hair active agents, sunscreens, viscosity modifiers, antibacterial agents, preservatives, pH adjusting agents, perfumes, sequestering agents, and mixtures thereof.

Non-limiting examples of film forming agents can be chosen from anionic compounds, non-ionic compounds, amphoteric compounds, zwitterionic compounds, proteins, viscosity modifiers, cationic polymers, polyamides, polyaminoamides, polyesters, silicone resins, polysaccharides, silicone fluids, polyacrylamides, starches, gums and mixtures thereof.

Non-limiting examples of conditioning agents include cationic conditioners such as quaternium-27, behenamidopropyl PG-dimonium chloride, hydroxyethyl tallowedimonium chloride, stearalkonium chloride and cetrimonium chloride. Other cationic conditioners may include those that are naturally derived.

Non-limiting examples of cationic polymers include hexadimethrine chloride, polyquaternium-4, polyquaternium-6, polyquaternium-7, polyquaternium-10, polyquaternium-11, polyquaternium-16, polyquaternium-22, polyquaternium- 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxyproyltrimonium chloride.

The at least one skin and hair active agent includes photoprotective agents, desquamating agents, depigmenting agents, moisturizing agents, skin lightening agents, anti-aging ingredients, anti-wrinkle agents, anti-dandruff agents and mixtures thereof. Non-limiting examples of the at least one skin active agent include α-hydroxy acids, β-hydroxy acids, α-keto acids, β-keto acids, retinoids, anthralins, anthranoids, peroxides, lithium salts, antimetabolites, vitamin D, antioxidants, ingredients that could promote moisturization and desquamating agents.

As skin and hair active agents that may be used in the composition of the present disclosure, examples that may be mentioned include moisturizers, for example, protein hydrolysates and polyols such as glycerol, glycols, for instance polyethylene glycols, and sugar derivatives; natural and plant extracts; anti-inflammatory agents; procyannidol oligomers; vitamins, for instance vitamin A (retinol), vitamin C (ascorbic acid), vitamin E (tocopherol), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; retinoids such as carotenoids and vitamin A derivatives; sunscreens; self-tanning agents; hydrocortisone; melatonin; algal, fungal, plant, yeast or bacterial extracts; enzymes; DHEA and its derivatives and metabolites; antibacterial active agents, for instance 2,4,4'-trichloro-2'-hydroxydi-phenyl ether (or Triclosan), 3,4,4'-trichloro-carbanilide (or Triclocarban) and the acids indicated above and especially salicylic acid and its derivatives; mattifying agents and mixtures thereof.

Preferred embodiments of the compositions of the present disclosure include skin active agents chosen from hydroxy acids, vitamins, sunscreens, UV filters, humectants, glycols, polyols, self-tanning ingredients, antioxidants and mixtures thereof.

Other preferred embodiments of the compositions of the present disclosure include skin active agents chosen from photoprotective agents, self-tanning agents, desquamating agents, depigmenting agents, moisturizing agents, skin lightening agents, anti-aging ingredients, anti-wrinkle agents, anti-dandruff agents and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of viscosity modifiers include water swellable/soluble cationic polymers from quaternized polysaccharides such as trimethyl ammonium substituted epoxide of hydroxyethyl cellulose, diallyldimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly(vinyl pyrrolidone/dimethyl amino ethylmethacrylate), poly(vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer.

Further suitable viscosity modifiers include anionic or nonionic polysaccharide polymers such as gum tragacanth, sodium or propylene glycol alginate, kappa-, iota-, or lambda-carrageenan, guar or hydroxylpropyl guar gum, karaya gum, gum arabic, locust bean gum, konjac mannan gum, gellan, xanthan, succinoglycan or its acidic or enzymatic hydrolysates, sodium carboxymethyl cellulose, methycellulose, hydroxylethylcellulose, hydroxypropylmethylcellulose, and hydroxypropylcellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Non-limiting examples of antibacterial agents include bacitracin, phenol, benzethonium chloride, erythromycin, neomycin, tetracycline, chlortetracycline and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

The at least one auxiliary ingredient is present in the composition in a preferred amount of from 0.001 to 50% and more preferably from 0.01 to 20% by weight, based on the total weight of the composition.

In particularly preferred embodiments of the present invention, the compositions are substantially free, that is, less than 0.25%, of silicones or sulfates. Further, a pH reading of the compositions ranges from about 3.5 to about 6.5, such as from about 4.0 to about 4.6.

Cosmetically Acceptable Carrier

The cosmetically acceptable carrier can be water and/or an organic solvent. Suitable organic solvents include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

The inventive composition can comprise a cosmetically acceptable carrier in the amount of about 95%, 90%, 80%, 70%, 60%, 50%, 40%, 30%, 20%, 10%, 5% or less based on the total weight of the composition. The composition can comprise a cosmetically acceptable carrier in the amount of about 5%, 10%, 20%, 30%, 40%, 50%, 60%, 70%, 80%, 90%, 95%, or more based on the total weight of the composition. Additionally, the amount of cosmetically acceptable carrier can be any combination of the above values, for example from about 20% to about 95%, or from about 50% to about 60% by weight based on the total weight of the compositions.

The compositions of the present invention contain water. The water is typically present in an amount from about 50 by weight to about 95% by weight, typically in an amount from about 55 by weight to about 90% by weight and more typically from about 60 by weight to 85% by weight, including all ranges and subranges there-between, based on the total weight of the composition.

A preferred embodiment of the present invention is a clear composition in the form of an oil-in-water microemulsion.

The compositions described above are useful as compositions for cleansing and conditioning keratinous substrates. These compositions include hair care products such as shampoos and conditioners, products for cleansing and conditioning skin such as skin cleansers and personal hygiene products and products for cleaning and conditioning lips and nails.

For example, when the keratinous substrate being treated is hair, the compositions of the present disclosure may impart shine and conditioning to the hair. The compositions of the present disclosure can also provide color retention properties to the artificial color in hair. In particular, the composition of the present disclosure may be provided in the form of a shampoo or rinse-out conditioner which preserves or inhibits the loss of artificial color in hair when the hair is subjected to one or more washings or shampooings.

Similar properties, along with styling, may be provided when the composition is in the form of a leave-on product.

The compositions of the present disclosure may also serve as a carrier vehicle for the auxiliary ingredients as described above.

When the keratinous substrate is skin, the compositions may impart protection from the sun (sunscreens) or provide skin benefits by serving as a carrier vehicle for skin actives (moisturizing agents, anti-acne agents, anti-wrinkle agents, anti-aging agents, depigmenting agents, whitening agents, etc.).

The method of treatment to be provided will depend on the keratinous substrate being targeted and, consequently, the specific ingredients contained in the composition used to effectuate the treatment. One of ordinary skill in the art will easily be able to determine these variables.

One preferred embodiment of the present invention is a clear cleansing composition comprising at least one alkoxylated monoamine, at least one alkoxylated monoacid, at least one lipophilic compound, at least one surfactant, optionally, at least one auxiliary ingredient and at least one cosmetically acceptable carrier in the form of a shampoo.

Another preferred embodiment of the present invention is a clear cleansing and conditioning composition comprising at least one alkoxylated monoamine, at least one alkoxylated monoacid, at least one lipophilic compound, at least one surfactant, optionally, at least one auxiliary ingredient and at least one cosmetically acceptable carrier in the form of a shampoo.

Another preferred embodiment of the present invention is a method of cleaning and conditioning keratinous substrates such as hair by applying a composition comprising at least one alkoxylated monoamine, at least one alkoxylated monoacid, at least one lipophilic compound, at least one surfactant, optionally, at least one auxiliary ingredient and at least one cosmetically acceptable carrier in the form of shampoo.

Another preferred embodiment of the present invention is a method of cleaning and conditioning keratinous substrates such as the skin by applying a composition comprising at least one alkoxylated monoamine, at least one alkoxylated monoacid, at least one lipophilic compound, at least one surfactant, optionally, at least one auxiliary ingredient and at least one cosmetically acceptable carrier in the form of a body wash.

Having described the subject matter of the present disclosure by way of illustration and example for purposes of clarity of understanding, it will be apparent to one of ordinary skill in the art that the same can be performed by modifying or changing the subject matter within a variety of conditions, formulations and other parameters without affecting its scope or any specific embodiment thereof, and that such modifications or changes are intended to be encompassed within the scope of the appended claims.

The following examples are for illustrative purposes only and are not intended to limit the scope of the claims.

EXAMPLES

| INCI NAME | EXAMPLE 1 | EXAMPLE 2 |
|---|---|---|
| LACTIC ACID | 0.45 | 0.45 |
| COCOS NUCIFERA (COCONUT) OIL | — | 1.00 |
| OLEA EUROPAEA (OLIVE) FRUIT OIL | 1.00 | — |
| FRAGRANCE | 0.60 | 0.60 |
| POLYMER | 0.70 | 0.70 |
| PRESERVATIVE | 0.70 | 0.70 |
| WATER | 79.8 | 79.8 |
| PEG-2 OLEAMINE | 1.00 | 1.00 |
| LAURETH-11 CARBOXYLIC ACID | 2.00 | 2.00 |
| SURFACTANTS | 13.75 | 13.75 |
| TOTAL | 100.00 | 100.00 |

| INCI NAME | EXAMPLE 3 | EXAMPLE 4 |
|---|---|---|
| LACTIC ACID | 0.45 | — |
| SQUALANE | 1.00 | — |
| PENTACLETHRA MACROLOBA SEED OIL | — | 0.50 |
| FRAGRANCE | 0.60 | 0.60 |
| POLYMER | 0.70 | 0.70 |
| PRESERVATIVE | 0.70 | 0.70 |
| WATER | 79.8 | 81.25 |

| -continued | | |
|---|---|---|
| PEG-2 OLEAMINE | 1.00 | 0.50 |
| LAURETH-11 CARBOXYLIC ACID | 2.00 | 2.00 |
| SURFACTANTS | 13.75 | 13.75 |
| TOTAL | 100.00 | 100.00 |

Procedure:
1. In the main kettle, mixed water and polymer until fully hydrated, and heated mixture to 60-65° C.
2. Added in the preservative and some surfactants and mixed for about thirty minutes until uniform.
3. Premixed the alkoxylated monoamine, alkoxylated monoacid and lipophilic compound and heated in a water bath to 60-65° C.
4. Added the premixed alkoxylated monoamine, alkoxylated monoacid and lipophilic compound to the main kettle and began cooling to 25° C.
5. Added remaining surfactants and continued cooling to 25° C.
6. At 40° C., added fragrance and mixed well.

These, examples were hair cleansing compositions that were clear in appearance and were tested on models in a salon. The examples demonstrated the following cosmetic and styling attributes: clean, shiny, soft, easy to detangle, not weighed down hair; good manageability, good body, volume, fullness; hair was smooth, without frizz, easy to blow dry; and had better defined curls.

COMPARATIVE EXAMPLES

Hair Cleansing Compositions that are hazy in appearance.

| INCI NAME | EXAMPLE 1 | EXAMPLE 2 | EXAMPLE 3 |
|---|---|---|---|
| LACTIC ACID | 0.45 | 0.45 | 0.45 |
| OLEA EUROPAEA (OLIVE) FRUIT OIL | 1.00 | 1.00 | 1.00 |
| FRAGRANCE | 0.60 | 0.60 | 0.60 |
| POLYMER | 0.70 | 0.70 | 0.70 |
| PRESERVATIVE | 0.70 | 0.70 | 0.70 |
| WATER | 80.8 | 79.8 | 81.8 |
| PEG-2 OLEAMINE | 1.00 | 2.00 | 0.25 |
| LAURETH-11 CARBOXYLIC ACID | 1.00 | 1.00 | 0.75 |
| SURFACTANTS | 13.75 | 13.75 | 13.75 |
| TOTAL | 100.00 | 100.00 | 100.00 |

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:
1. A clear composition, comprising:
(a) from about 0.1 to about 4% by weight of the composition of at least one alkoxylated monoamine comprising PEG-2 Oleamine;
(b) from about 0.1 to about 6% by weight of the composition of at least one alkoxylated monoacid comprising Laureth-11 Carboxylic Acid;
(c) from about 0.1% to about 2% by weight of the composition of at least one lipophilic compound comprising a plant oil;
(d) from about 5% to about 30% by weight of the composition of at least one anionic surfactant chosen from alkyl sulfonates, alkyl ether sulfonates, sulfate esters of an alkylphenoxy polyoxyethylene ethanol, alpha-olefin sulfonates, beta alkyloxy alkene sulfonates, alkyl aryl-sulfonates, alkyl carbonates, succinamates, sulfosuccinates, sarcosinates, octoxynol or nonoxynol phosphates, taurates, fatty taurides, sulfated monoglycerides, isethionates and mixtures thereof;
(e) optionally, at least one auxiliary ingredient; and
(f) at least one cosmetically acceptable carrier comprising water;
wherein the ratio by weight of (b):(a) is 2:1;
wherein the ratio by weight of (a)+(b):(c) is greater than 2;
wherein the ratio by weight of (a) to (c) is about 1;
wherein the amount of (c) is exclusive of any fragrance that may be present in the composition; and wherein the composition does not contain nonionic surfactants.

2. The composition of claim 1, wherein the composition further comprises surfactants chosen from amphoteric surfactants, zwitterionic surfactants, and mixtures thereof.

3. The composition of claim 1, wherein (e) is present and is chosen from film forming agents, proteins, amino acids, cationic polymers, viscosity modifiers, antibacterial agents, sunscreens, preservatives, pH adjusting agents, perfumes, sequestering agents, skin and hair active agents, and mixtures thereof.

4. The composition of claim 3, wherein (e) is present in an amount of from about 0.001 to 50% by weight, based on the total weight of the composition.

5. The composition of claim 1, wherein (f) is present in an amount from about 50% to about 95% by weight, based on the total weight of the composition.

6. The composition of claim 1, wherein the ratio by weight of (b):(a):(c) is 2:1:1.

7. The composition of claim 1, wherein the composition is sulfate free.

8. A method of cleansing and conditioning a keratinous substrate comprising:
(a) providing a composition comprising:
(i) from about 0.1 to about 4% by weight of the composition of at least one alkoxylated monoamine comprising PEG-2 Oleamine;
(ii) from about 0.1 to about 6% by weight of the composition of at least one alkoxylated monoacid comprising Laureth-11 Carboxylic Acid;
(iii) from about 0.3% to about 1.5% by weight of the composition of at least one lipophilic compound comprising a plant oil;

(iv) from about 5% to about 30% by weight of the composition of at least one anionic surfactant chosen from alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, succinamates, sulfosuccinates, sarcosinates, octoxynol or nonoxynol phosphates, taurates, fatty taurides, sulfated monoglycerides, isethionates and mixtures thereof;

(v) optionally, at least one auxiliary ingredient;

(vi) at least one cosmetically acceptable carrier comprising water;

wherein the ratio by weight of (ii):(i) is from 2:1;

wherein the ratio by weight of (i)+(ii):(iii) is greater than 2;

wherein the ratio by weight of (i) to (iii) is about 1;

wherein the amount of (iii) is exclusive of any fragrance that may be present in the composition;

(b) applying said composition; and wherein the composition does not contain nonionic surfactants onto the keratinous substrate.

9. The composition of claim 8, wherein the ratio by weight of (b):(a):(c) is at about 2:1:1.

* * * * *